United States Patent [19]
Mandel

[11] Patent Number: 5,269,322
[45] Date of Patent: Dec. 14, 1993

[54] LOWER BACK AND SPINAL STRESS REDUCER APPARATUS

[76] Inventor: Edward Mandel, 3109 Lakeshore Drive, Deerfield Beach, Fla. 33442

[21] Appl. No.: 973,830

[22] Filed: Nov. 9, 1992

[51] Int. Cl.⁵ .......... A61G 15/00; A61F 5/37; A61F 5/00; A47C 20/02
[52] U.S. Cl. .................. 128/845; 128/882; 602/23; 602/26; 5/648; 5/650
[58] Field of Search .......... 128/869, 846, 875, 876, 128/877–878; 602/19, 5, 20, 23–29, 35–36, 62, 63, 65; 5/648–650, 624; 2/16, 22

[56] References Cited
U.S. PATENT DOCUMENTS

| | | | |
|---|---|---|---|
| 3,831,467 | 8/1974 | Moore | 602/26 |
| 4,111,194 | 9/1978 | Cox | 602/26 |
| 4,177,806 | 12/1979 | Griffin | 128/132 R |
| 4,186,738 | 2/1980 | Schleicher | 602/23 |
| 4,390,015 | 6/1983 | Clements | 128/80 R |
| 4,584,730 | 4/1986 | Rajan | 5/431 |
| 4,607,628 | 8/1986 | Dashefsky | 602/26 |
| 4,706,302 | 11/1987 | Padfield | 2/22 |
| 4,736,477 | 4/1988 | Moore | 5/443 |
| 4,754,510 | 7/1988 | King | 5/431 |
| 4,905,715 | 3/1990 | Johnson | 128/882 |
| 4,926,884 | 5/1990 | Lonardo | 128/892 |
| 5,073,986 | 12/1991 | Farrago | 2/22 |
| 5,083,575 | 1/1992 | Jones | 128/877 |

*Primary Examiner*—Michael A. Brown
*Attorney, Agent, or Firm*—McHale & Slavin

[57] ABSTRACT

The leg separating apparatus (10) is a bifurcated relatively deformable and resilient foam or plastic structure for placement on the inner surface of a patient's leg. The apparatus provides predetermined leg separation to alleviate the stress placed upon the spine and lower back of a patient when the patient is in a lying position. A centrally located knee shroud (12) provides a knee bone centering portion (20) for an opposing knee. Traverse support members (22, 36) extend from each side of the knee shroud to distribute the associated leg weight along the length of the leg. Straps (50) secure the support members (22, 36) to the leg. Each support member includes an accordion segmented portion (34, 46) allowing the leg separating structure to bend during the sleeping hours and eliminates the need for removal for short walks. An alternative embodiment set forth a shell structure with a rotatable knee shroud.

19 Claims, 3 Drawing Sheets

LOWER BACK AND SPINAL STRESS REDUCER APPARATUS

FIELD OF THE INVENTION

The present invention relates generally to devices used in the medical field for the reduction of lower back and spinal stress and, more particularly, to an apparatus for separating a patient's legs in a non-locked yet predetermined spacial distance for correct posturing of a patient's legs while in a lying position.

BACKGROUND INFORMATION

It is well known that positioning a patient in a lateral decumbent posture places a stress upon the spine and general lower back area. This stress may lead to extreme discomfort if the patient suffers from a spinal disorder, discongenic disease, old age, and so forth. It is also well known that the discomfort during resting periods can be reduced or eliminated if the legs are separated a predetermined distance, a distance typically measured between the knees. For instance, many women rely upon a pillow placed between the knees for sleeping assistance during pregnancy, the leg separation easing the discomfort on the lower back. Similarly, elderly or patients suffering from arthritis of the hips find a benefit in leg separation during sleep by placing the legs in their normal spaced apart position found during an upright stance.

In an effort to accommodate the positioning problem, numerous prior art devices have been set forth. The typical prior art device is directed to a pad placed between the knees. The pad is typically a variation of a conventional pillow which is strapped to a patient's inner leg to maintain its placement. The modified pillow has a number of disadvantages including sterilization, heat buildup at the point of skin contact, skin irritation due to moisture, and strapping means that do not permit articulation at the knee, all of which can lead to chaffing or bed sores. In addition, improper strapping prevents the patient from walking, a point of difficulty if the patient needs to use a washroom in the middle of the night.

U.S. Pat. No. 4,177,806 issued to Griffin discloses a knee pillow that is comprised of a pad strapped to the knee of a patient. The Griffin device provides a cushion between the knees for the purpose of preventing a patient's knees from digging into each other. The Griffin device is typical of the art in that the pad may allow walking but to the expense of skin irritation. The padding places all of the leg weight directly upon the knee bones.

U.S. Pat. No. 4,390,015 issued to Clement's discloses a thigh support brace to immobilize a patient's thigh while in bed. A detachable bracket allows removal for walking, however, replacement of the bracket by an elderly patient is extremely difficult. In addition, complete immobilizing of the legs during sleep need only be performed for certain types of patients and may lead to discomfort for others.

U.S. Pat. No. 4,706,302 issued to Padfield discloses a comfort pad that is strapped to a patient's legs. The pad acts as a cushion to relieve pressure when the patient is sleeping on their side. This pad also places all of the leg weight directly upon the knee bones.

U.S. Pat. No. 4,736,477 issued to Moore discloses a knee pillow that is strapped to the leg. The knee pillow has a series of notches which allows the knee to bend for the prevention of chaffing. However, the notches lead to an unpredictable spacing of the leg. If two such devices are employed, walking is inhibited for the interference locking of notches can cause the patient to stumble.

U.S. Pat. No. 4,584,730 issued to Rajan discloses a device for stabilizing the pelvis of a patient through the use of a preformed device. The device will not allow the patient to walk or rotate during sleep.

U.S. Pat. No. 4,754,510 issued to King discloses a body pillow that provides leg separation and is held in position by the patient's upper body.

U.S. Pat. No. 4,905,715 issued to Johnson discloses a padded leg guard that wraps about the knee to help prevent inner leg skin irritation.

U.S. Pat. No. 4,910,818 issued to Grabill discloses a leg positioning assembly to maintain the legs of the patient in a side or back position.

U.S. Pat. No. 4,926,884 issued to Lonardo discloses a leg positioning device to help prevent skin irritation during leg separation. The Lonardo device sets forth padding that extends along the length of the patients inner leg.

Thus, what is lacking in the art is a leg separating apparatus or device that provides leg weight pressure distribution along the length of the patient's leg, allows movement of the legs during sleep without dislodgement or separation from the legs, permits articulation at the knee, allowing the patient to walk without removing the device or causing skin irritation. Finally, the apparatus should allow the use of disposable or cleanable covers without the need for cleaning the underlying device.

SUMMARY OF THE INVENTION

The instant invention satisfies the aforementioned needs by disclosing an apparatus for attachment to the inner surface of the leg of a patient. The apparatus maintains a predetermined distance between the patient's legs when the patient is in a lateral decumbent posture reducing the stress upon the patient's spine and lower back area.

In general, the invention is a bifurcated relatively deformable, resilient, molded structure having a centrally disposed knee shroud. An upper traverse support member is coupled to one end of the knee shroud for distribution of pressure and securement to the thigh of the patient. A lower traverse support member is coupled to the other end of the knee shroud. The lower support member provides distribution of pressure and securement to the calf of the patient. Each support member includes the use of an accordion shape to permit articulation of the structure. The knee shroud includes a self centering indentation for fixation upon the protruding knee bone of the adjacent leg. Alternative embodiments teach the use of various means for knee shroud articulation.

Accordingly, a primary object of the present invention is to provide an apparatus that attaches to the inner side of a patient's leg to provide separation of the legs without padding of the knee bone to relieve the stress placed upon the lower back when the patient is lying in a lateral sideward position.

Still another object of the present invention is to provide a knee separation device constructed of foam or plastic that is shaped to the contour of the leg with sufficient rigidity to distribute weight along the length of the patient's thigh and calf.

Yet still another object of the present invention is to provide accordion segmentation over the thigh and calf supports to accommodate muscle movement and bending along a common axis.

Another object of the present invention is to provide an articulating knee bone cover, the cover maintaining a fixed distance between the knees without placing pressure upon the knee bone cover.

Still another object of the present invention is to provide a device that allows the patient to take short walks without removal.

Another object of the present invention is to provide that is economical to manufacture and uses a soft, flexible, and resilient machine washable cover for ease of cleaning.

Yet still another object of the present invention is to provide a knee bone centering device for use when two devices are employed, the device aligning the knees in a predetermined position.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
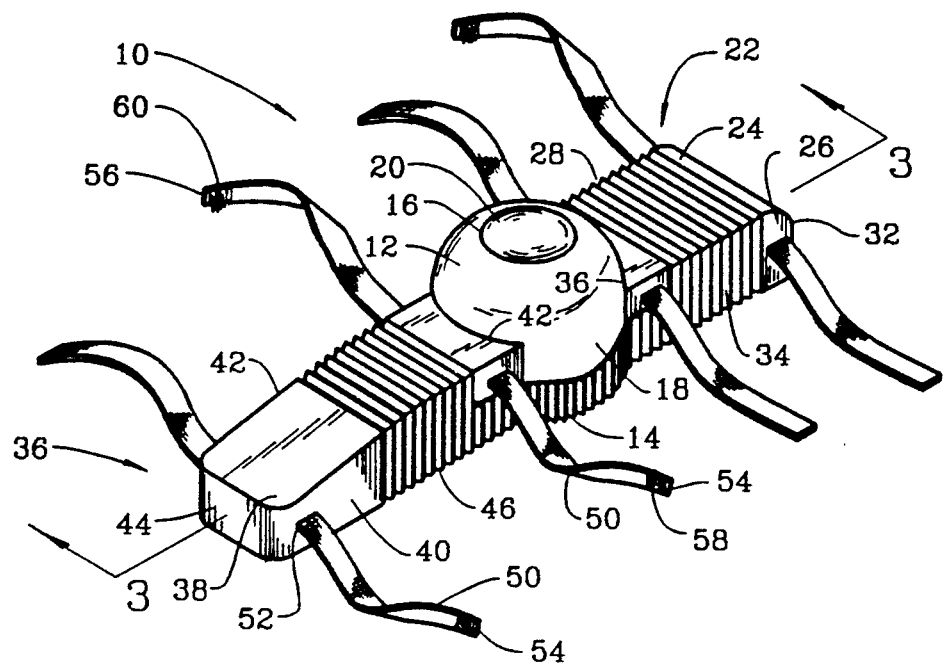
FIG. 1 is a perspective view showing the foam leg separator according to the present invention having a full length accordion segmentation.

Now referring to FIG. 1, shown is the preferred embodiment of the leg separator of the instant invention generally depicted by numeral 10. The leg separator 10 set forth is a bifurcated relatively deformable, resilient, molded structure constructed of a medium density solid foam material having an overall length of about 17 inches extending along a longitudinal axis residing within a plane. The leg separator 10 has a centrally disposed knee shroud 12 leading to a height found at indentation lip 16. The outer surface 18 of the knee shroud 12 forming a substantially circular structure having approximately a 4 inch diameter. A preformed indentation 20 is located on the top of the knee shroud 12 depending downwardly from lip 16 providing a location for the adjoining leg knee bone, the indentation 20 accepting the knee bone without placing pressure directly thereon.

A substantially rectangular upper traverse support member 22 having a top surface 24 with two opposing side walls 26, 28 depending downwardly to the common inner surface 14 and extending outwardly from a proximal end 30 coupled to the knee shroud 12 to a first distal end wall 32. The end wall 32 attached to said upper support walls and said upper support top wall by an oblique curvature from top surface 24 downwardly along a portion of support member 22. The distal end wall 32 extending approximately 6½ inches from the center of knee shroud 12. An accordion wall shape 34 is placed along at least a portion of the length of the upper support member 22. The accordion shape provides foam and plastic construction with an even greater amount of flexibility. The accordion allows the material to fold upon itself with limited resistance.

A substantially rectangular lower traverse support member 36 having a top wall 38 with two opposing side walls 40, 42 depending downwardly to the common inner surface 14 and extending inwardly from a proximal end 42 coupled to the knee shroud 12 to distal end wall 44. The distal end wall 44 is attached to said lower support walls 40,42 and the lower support top wall 38 by an oblique curvature. The distal end wall 44 is approximately 12 inches from the center of the knee shroud 12. An accordion shape 46 is molded along at least a portion of the length of the lower support member 36. The accordion shaped ridges are preferably placed along the bottom of the knee shroud 12 providing flexibility across the length of the structure.

A plurality of substantially identical straps 50 are made available for insertion into and through each of a series of strap slots 52. Each strap having a first end 54 and a second end 56 and two side surfaces. The length of the strap is sized to accommodate a human leg. The ends of the strap couple to each other by tying, buckles, snaps, or the preferred embodiment of pile 58 and loop 60 attachment.

Figure 2:
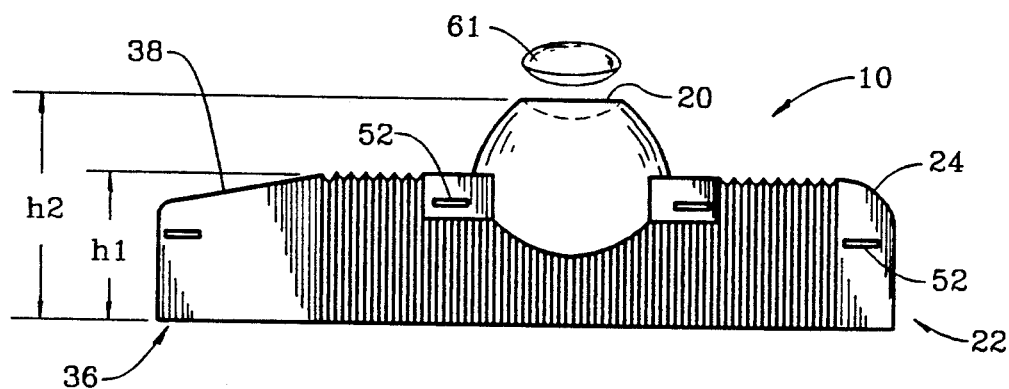
FIG. 2 is a side elevational view of FIG. 1.

Now referring to FIG. 2, shown is a side view of the leg separator 10 without straps. The figure depicts strap slots 52 placed in side walls 26 and 40. The curvature 24 of the upper member 22 is shown, the curvature allows the legs to raise to a height $h_1$ of 2 inches. The actual knee separation provided by the raised knee shroud 12 has a combined height $h_2$ of 3½ inches. The curvature 38 of lower support 36 provides calf support for the opposite leg while tapering to the ankle area. An option available to the instant invention is the use of an alignment ring 61 for frictional insertion into indentation 20. The alignment ring 61 is used when two leg separators are employed, the alignment ring 61, engagable with the second leg separator, locks the knees but not the feet in a fixed position.

Figure 3:
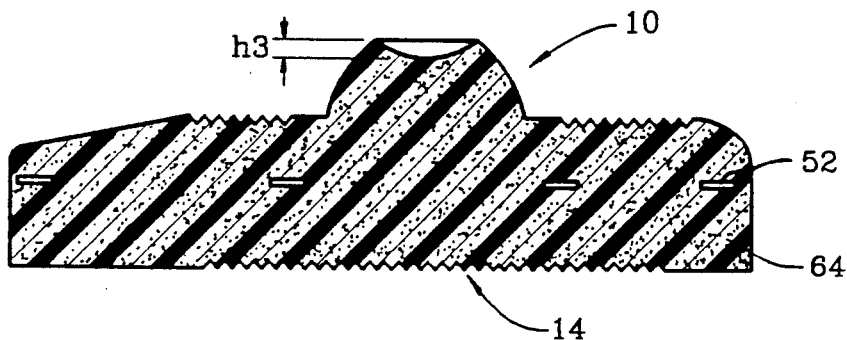
FIG. 3 is a cross sectional of FIG. 2.
Figure 4:
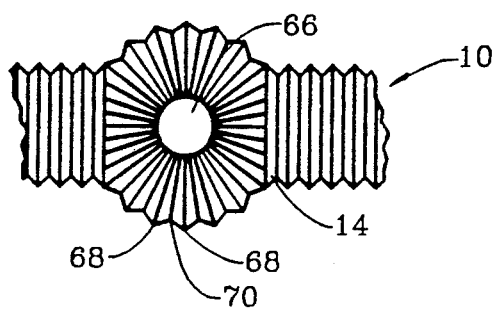
FIG. 4 is a bottom view of FIG. 1.

FIG. 3 is a cross sectional view of the leg separator constructed of solid foam 64. The accordion ridges 14 are placed across the bottom of the structure allowing the apparatus to compress the ridges. The strap slots 52 are shown extending through the foam section. FIG. 4 is a bottom view of the leg separator illustrating the radially extending ridges projecting from the center 66. When the foam is bent, ridges 68 are allowed to fold toward each other collapsing the fold depicted by numeral 70.

Figure 5:
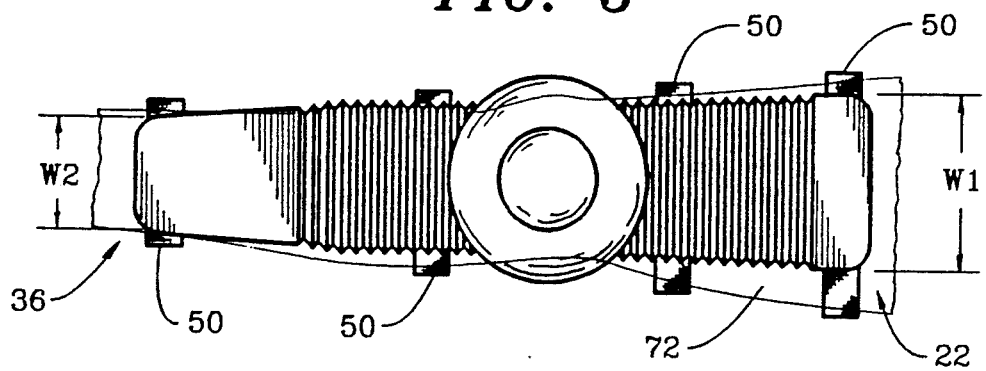
FIG. 5 is a top view of FIG. 1 showing the leg separator attached to the inner leg of a patient.

Now referring to FIG. 5, the structure 12 is shown attached to the inner side leg 72 by use of the flexible straps 50. The straps are placed at areas of the leg that are not susceptible to a large range of movement. The width $w_1$ of the upper portion 22 is approximately 4 inches which tapers down to a width $w_2$ of approximately 1½ inches at lower portion 36.

A removable cover 200 having a plurality of strap slots corresponding to the leg separator slots 52, can be used to encompass the structure with a soft material. Once installed, the cover 200 is aligned to the slots allowing insertion of the straps for combination securement to the patient's inner leg. The cover 200 is easily removed for cleaning thus preventing the need for sterilizing the leg separator after each use.

Figure 6:
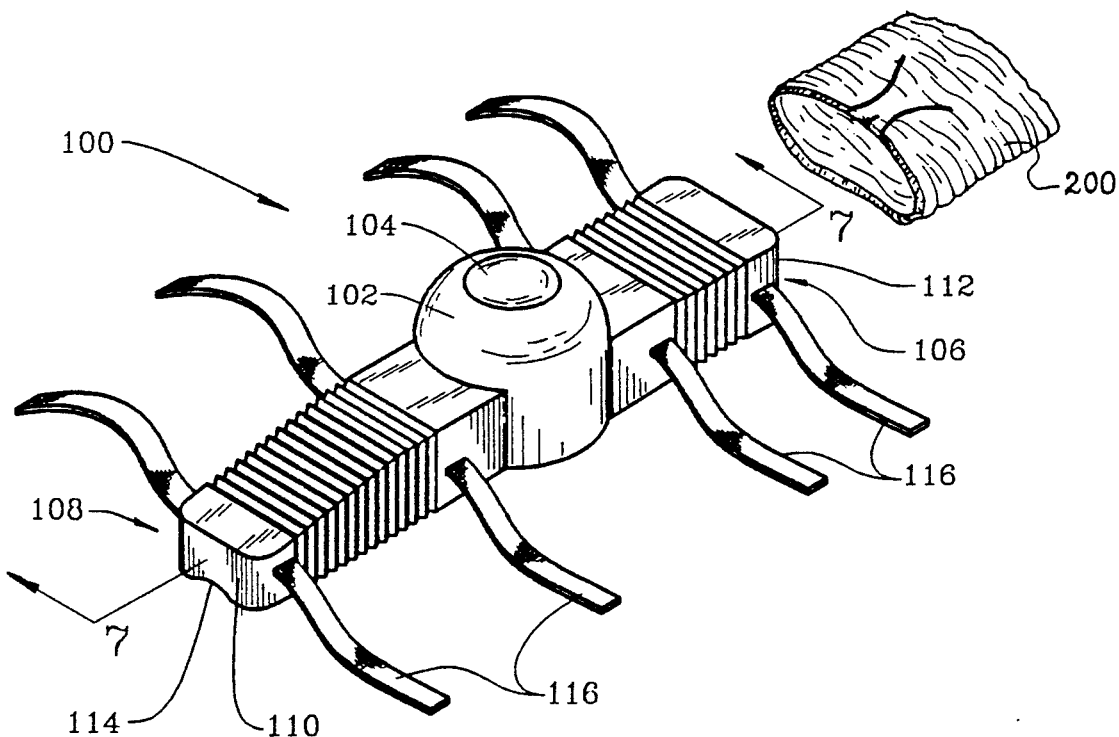
FIG. 6 is a perspective view showing an alternative plastic shell embodiment of the present invention having a partial length accordion segmentation.

Now referring to FIG. 6, shown is an alternative embodiment of the leg separator generally depicted by numeral 100. The leg separator is similar to the previously described embodiment except the instant embodiment is constructed of a plastic shell. The leg separator 100 includes the centrally disposed knee shroud 102 having knee bone indentation 104. The outer surface of the knee shroud maintains a substantially circular outer diameter.

The substantially rectangular upper traverse support member 106 is similar to the above described and provides a top surface with two opposing side walls depending downwardly to a common inner surface, not shown. The interior surface forming a hollow chamber along the length of the housing. Similarly, a substantially rectangular lower traverse support 108 is provided having a top surface with two opposing side walls depending downwardly to the common inner surface.

The end wall 110 of lower support member 108 and 112 of upper support member 106 employ a mirror image curvature 114 to eliminate a pressure point when using plastic or higher density foam. A cover 200 is placed over the housing 100 allowing the straps 116 to protrude therethrough. A correctly fitting cover 200 provides a taunt structure capable of following the curvature 114 when strapped to the patient's leg. The material forming the bottom surface of the cover 200 distributes the majority of weight placed upon the structure directly to the leg.

Figure 7:
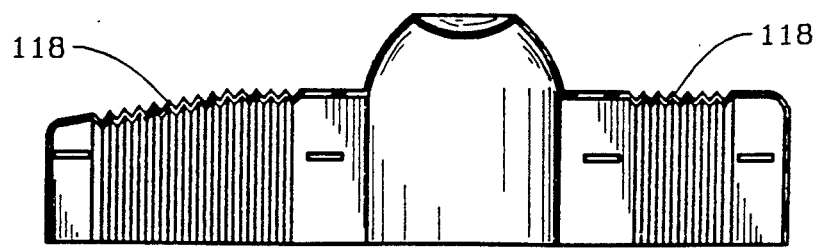
FIG. 7 is a cross sectional side view of FIG. 6.

FIG. 7 is a cross section view of FIG. 6 illustrating the hollow shell. Similarly to foam embodiment described above, it has been found that the use of accordion ridges 118 along at least a portion of the upper member 106 and/or lower member 108 provides the apparatus with a means for bending near the knee with minimum resistance.

Figure 8:
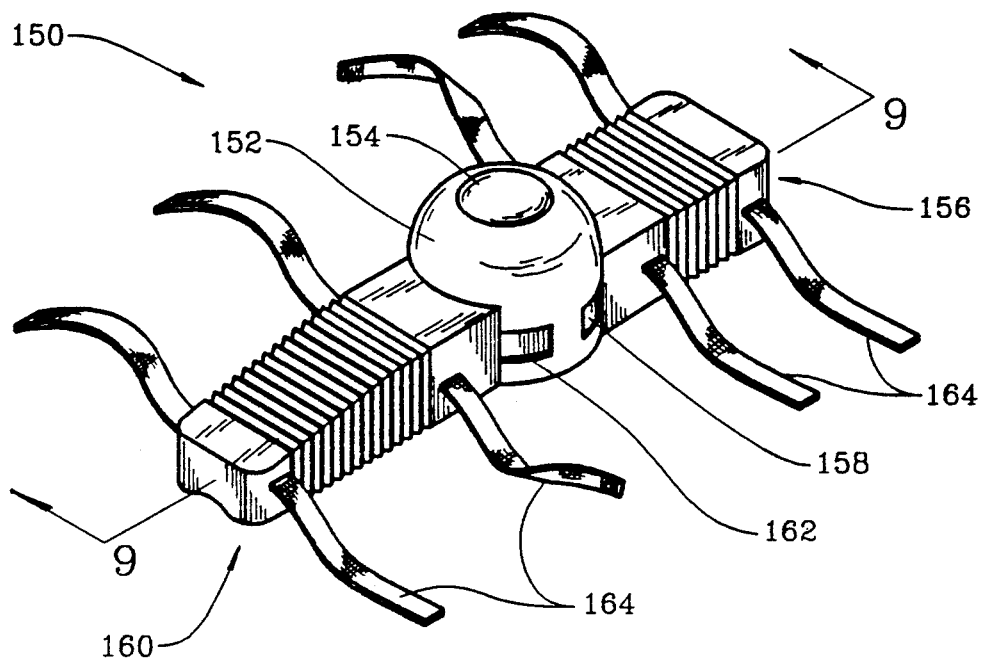
FIG. 8 is a perspective view showing an alternative embodiment of the present invention having a partial length accordion segmentation and articulating knee shroud.

Now referring to FIG. 8, shown is a third embodiment of the leg separator generally depicted by numeral 150. The leg separator 150 is similar to the previously described embodiment except the instant embodiment can be constructed of foam, plastic, or a combination of the two materials. The leg separator 150 includes the centrally disposed knee shroud 152 with knee indentation 154 The outer surface of the knee shroud retains a substantially circular outer diameter. Unique to this embodiment is the use of a slotted knee shroud wherein the upper traverse support member 156 is slidably engaged with the shroud 152 by use of slot 158. The shroud 152 can be made of plastic and the upper support member 156 of foam or the materials reversed. The foam having a T-shape or the like slot engaging attachment. The lower traverse support member 160 can also be made to slidably engage with the shroud 152 by use of slot 162. Members 156 and 160 can be detached from the structure for a particular application, i.e. thigh and knee support only, or used individually. Straps 164 allow the structure to be attached to the patient's leg in the same manner as previously mentioned.

Figure 9:
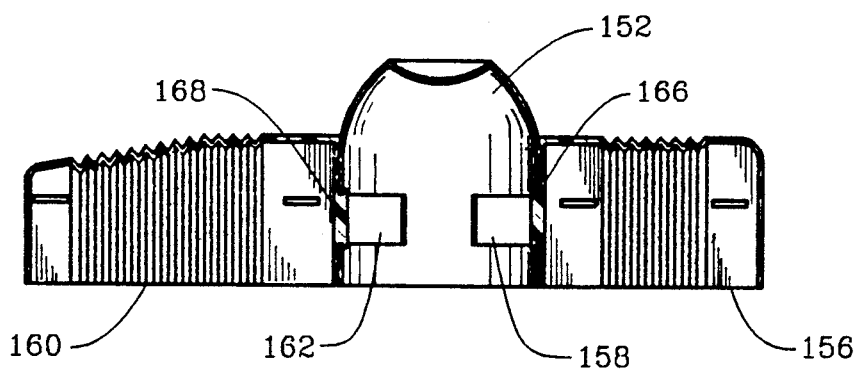
FIG. 9 is a cross sectional side view of FIG. 8.

FIG. 9 is a cross sectional view of FIG. 8 illustrating rotational ability of the upper and lower members in relation to the knee shroud. The T-shaped attachment 166 is operatively associated with the slotted opening 158 allowing the upper member to rotate along the length of the slot 158. Similarly, T-shaped attachment 168 is operatively associated with the slotted opening 162 allowing the upper member to rotate along the length of the slot 162.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification. Various knee shroud attachments and means for articulation are deemed within the scope of this invention.

What I claim is:

1. A lower back and spine stress reduction apparatus for attachment to the inner leg portion of a patient for maintaining a predetermined distance between the patient's legs when the patient is in a lying position, said apparatus comprising: a bifurcated relatively deformable, resilient, molded structure having a length and a common inner surface extending along a longitudinal axis residing within a plane, said structure comprising; a centrally disposed knee shroud, said knee shroud having a height and a width formed by a substantially circular outer surface leading to said common inner surface; means for centering said knee shroud over a knee bone; a substantially rectangular upper traverse support member having a top surface with two opposing side walls depending downwardly to said common inner surface and extending outwardly from a proximal end coupled to said knee shroud to a first distal end wall, said first distal end wall placed a first distance from said proximal end; a substantially rectangular lower traverse support member having a top wall with two opposing side walls depending downwardly to said common inner surface and extending inwardly from a proximal end coupled to said knee shroud to a second distal end wall, said second distal end wall placed a second distance from said proximal end; and a means for securing said common inner surface of said bifurcated structure to a patient's inner leg; whereby said structure is secured to the patient's inner leg providing a predetermined distance between the patient's legs while in a lying position thereby distributing associated leg weight along the length of the patient's leg.

2. The apparatus according to claim 1 wherein said structure is constructed of a medium density solid foam material.

3. The apparatus according to claim 1 wherein said structure is constructed of lightweight formable plastic.

4. The apparatus according to claim 1 wherein said upper support member includes an articulating means.

5. The apparatus according to claim 4 wherein said articulating means is defined as an accordion shape wall formation along at least a portion of the length of said upper support member.

6. The apparatus according to claim 4 wherein said articulating means is defined as slidable hinge between said upper support member and said centrally disposed knee shroud.

7. The apparatus according to claim 1 wherein said lower support member includes an articulating means.

8. The apparatus according to claim 7 wherein said articulating means is defined as an accordion shape wall formation along at least a portion of the length of said lower support member.

9. The apparatus according to claim 7 wherein said articulating means is defined as slidable hinge between said lower support member and said centrally disposed knee shroud.

10. The apparatus according to claim 1 wherein said means for securing said common inner surface of said bifurcated structure to a patient's inner leg includes said upper member side walls having a plurality of fluidly communicated opposing strap slots, said strap slots receptive to a strapping means.

11. The apparatus according to claim 10 wherein said strap slots are further defined as a first pair of communicated strap slots disposed adjacent to said proximal end and a second pair of communicated opposing strap slots disposed adjacent to said first distal end wall, said lower member side walls having a third pair of communicated opposing strap slots disposed adjacent to said proximal end and a forth pair of communicated opposing strap slots disposed adjacent to said second distal end wall.

12. The apparatus according to claim 10 wherein said strapping means is defined as a plurality of substantially identical straps for removable insertion into and through each of said strap slots, each strap comprising a first end and a second end and two side surfaces, said first end separated from said second end a predetermined distance sized to accommodate a human leg, said first and second end having a means for coupling together.

13. The apparatus according to claim 12 wherein said means for coupling comprise a loop and pile fastener attached to at least one side surface of said first and second end of each of said straps.

14. The apparatus according to claim 1 wherein said means for centering said knee shroud over a knee bone is further defined as a preformed indentation on the outer surface of said knee shroud.

15. The apparatus according to claim 1 wherein said means for centering said knee shroud over a knee bone is further defined as an alignment ring insertable into a preformed indentation of said knee shroud.

16. The apparatus according to claim 1 wherein said apparatus includes a removable cover for placement over said structure.

17. A lower back and spine stress reduction apparatus for attachment to the inner leg portion of a patient for maintaining a predetermined distance between the patient's legs when the patient is in a lying position, said apparatus comprising: a bifurcated relatively deformable, resilient, molded structure constructed of a medium density solid foam material having a length and a common inner surface extending along a longitudinal axis residing within a plane, said structure comprising; a centrally disposed knee shroud, said knee shroud having a height and a width formed by a substantially circular outer surface leading to said common inner surface, said outer surface having a preformed indentation for centering of the structure to a knee bone; a substantially rectangular upper traverse support member having a top surface with two opposing side walls depending downwardly to said common inner surface and extending outwardly from a proximal end coupled to said knee shroud to a first distal end wall, said first distal end wall attached to said upper support walls and said upper support top wall by an oblique curvature, said first distal end wall placed a first distance from said proximal end with an accordion shaped wall segment disposed along at least a portion of said upper support member; a substantially rectangular lower traverse support member having a top wall with two opposing side walls depending downwardly to said common inner surface and extending inwardly from a proximal end coupled to said knee shroud to a second distal end wall, said second distal end wall attached to said lower support walls and said lower support top wall by an oblique curvature, said second distal end wall placed a second distance from said proximal end with an accordion shaped wall segment disposed along at least a portion of said lower support member; a plurality of fluidly communicated opposing structure strap slots disposed in said member side walls; a plurality of substantially identical straps for removable insertion into and through each of said strap slots, each strap comprising a first end and a second end and two side surfaces, said first end separated from said second end a predetermined distance sized to accommodate a human leg, said first and second end having a means for coupling together; and a removable cover having a plurality of strap slots corresponding to said structure strap slots, said cover available for placement over said structure;

whereby said cover is placed over said structure for alignment of said strap slots wherein said structure is secured to the patient's inner leg by placing said straps through said strap slots for coupling each end of the strap about the patient's leg, said structure providing a predetermined distance between the patient's legs while in a lying position thereby distributing associated leg weight along the length of the patient's leg.

18. The apparatus according to claim 17 wherein said means for coupling comprise a loop and pile fastener attached to at least one side surface of said first and second end of each of said straps.

19. A lower back and spine stress reduction apparatus for attachment to the inner leg portion of a patient for maintaining a predetermined distance between the patient's legs when the patient is in a lying position, said apparatus comprising: a bifurcated relatively deformable, resilient, molded structure constructed of a plastic shell having a length and an inner surface, said structure comprising; a centrally disposed knee shroud, said knee shroud having a height and a width formed by a substantially circular outer surface leading to said common inner surface, said outer surface having a preformed indentation for self-centering of the structure to a knee bone; a substantially rectangular upper traverse support member having a top surface with two opposing side walls depending downwardly to said common inner surface and extending outwardly from a proximal end coupled to said knee shroud to a first distal end wall, said first distal end wall attached to said upper support walls and said upper support top wall by an oblique curvature, said first distal end wall placed a first distance from said proximal end; a substantially rectangular lower traverse support member having a top wall with two opposing side walls depending downwardly to said common inner surface and extending inwardly from a proximal end coupled to said knee shroud to a second distal end wall, said second distal end wall attached to said lower support walls and said lower support top wall by an oblique curvature, said second distal end wall placed a second distance from said proximal end; articulating means between said knee shroud and said upper and said lower support members; a plurality of fluidly communicated opposing strap slots disposed in said member side walls; a plurality of substantially identical straps for removable insertion into and through each of said strap slots, each strap comprising a first end and a second end and two side surfaces, said first end separated from said second end a predetermined distance sized to accommodate a human leg, said first and second end having a means for coupling together; and a removable cover having a plurality of strap slots corresponding to said structure strap slots, said cover available for placement over said structure providing a flexible bottom wall across the bottom of said member support walls;

whereby said cover is placed over said structure for alignment of said strap slots wherein said structure is secured to the patient's inner leg by placing said straps through said strap slots for coupling each end of the strap about the patient's leg, said cover forming said bottom wall biasing said structure against the patient's leg providing a predetermined distance between the patient's legs while in a lying position thereby distributing associated leg weight along the length of the patient's leg.

* * * * *